US006991816B2

(12) United States Patent
Esperester et al.

(10) Patent No.: US 6,991,816 B2
(45) Date of Patent: Jan. 31, 2006

(54) COMPOSITION FOR TREATING CHRONIC VENOUS INSUFFICIENCIES USING AN EXTRACT OF RED VINE LEAVES

(75) Inventors: Anke Esperester, Mainz (DE); Hans W. Frey, Ockenheim (DE); Jean-Michel Vix, Weisbaden (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 129 days.

(21) Appl. No.: 10/675,630

(22) Filed: Sep. 30, 2003

(65) Prior Publication Data
US 2004/0062824 A1    Apr. 1, 2004

Related U.S. Application Data

(60) Continuation of application No. 10/262,703, filed on Oct. 2, 2002, now abandoned, which is a division of application No. 09/691,003, filed on Oct. 18, 2000, now Pat. No. 6,485,727.

(60) Provisional application No. 60/160,518, filed on Oct. 20, 1999.

(51) Int. Cl.
*A61K 35/78* (2006.01)
(52) U.S. Cl. .................. 424/766; 424/774; 514/929
(58) Field of Classification Search ............... 424/766, 424/774; 514/929
See application file for complete search history.

(56) References Cited

U.S. PATENT DOCUMENTS

| | | | | |
|---|---|---|---|---|
| 3,136,693 A | * | 6/1964 | Abeles ...................... 424/766 |
| 5,107,000 A | | 4/1992 | Lunder | |
| 5,780,060 A | * | 7/1998 | Levy et al. ................. 424/489 |
| 6,485,727 B1 | * | 11/2002 | Esperester et al. .......... 424/774 |
| 6,627,231 B2 | * | 9/2003 | Soldati ...................... 424/766 |
| 6,835,401 B2 | * | 12/2004 | Soldati ...................... 424/766 |
| 2003/0007988 A1 | * | 1/2003 | Courtin ..................... 424/401 |
| 2004/0151769 A1 | * | 8/2004 | Esperester et al. .......... 424/465 |

FOREIGN PATENT DOCUMENTS

| | | |
|---|---|---|
| EP | 0 694 305 | 1/1996 |
| GB | 934 554 | 8/1963 |
| WO | WO 99 29331 | 6/1999 |

OTHER PUBLICATIONS

Girre et al. Fitoterrapia. 1990. vol. 61, No. 3, pp. 201-206, BIOSIS Abstract enclosed.*

Girre, L. et al: "In Vitro Antiherpetic Activity of the leaves of the Red Vine Vitis-Vinifera" Fitoterapia., vol. 61, No. 3, 1990, pp. 201-206, XP000981757 IDB Holding, Milan., IT ISSN: 0367-326 p. 201-202.

Database Medline: Online US National Library of Medicine (NLM) Bethesda MD US: Constantini, A. et al: "Clinical and capillaroscopic evaluation of chronic uncomlicated venous insufficiency with procyanidins extracted from citis vinifera" XP002159795.

* cited by examiner

*Primary Examiner*—Christopher R. Tate
(74) *Attorney, Agent, or Firm*—Michael P. Morris; Thomas C. Blankinship; Timothy X. Witkowski

(57) ABSTRACT

The invention relates to a dietary supplement consisting of an aqueous extract of red vine leaves and an acceptable carrier which prevents and reduces the discomfort relating to mild-to-moderate chronic venous insufficiency of the legs.

8 Claims, No Drawings

COMPOSITION FOR TREATING CHRONIC VENOUS INSUFFICIENCIES USING AN EXTRACT OF RED VINE LEAVES

RELATED APPLICATION DATA

This application is a continuation of U.S. application Ser. No. 10/262,703, filed Oct. 2, 2002, now abandoned which is a divisional of U.S. application Ser. No. 09/691,003, filed Oct. 18, 2000, now U.S. Pat. No. 6,485,727 both of which claim, as does the present application, priority benefit to U.S. Provisional Application Ser. No. 60/160,518 filed Oct. 20, 1999, the disclosures of all of which are incorporated by reference in their entirety.

TECHNICAL FIELD OF THE INVENTION

The present invention relates to a dietary supplement, and more particularly, to a dietary supplement for preventing or alleviating the discomfort associated with mild-to-moderate chronic venous insufficiency of the lower extremities.

BACKGROUND OF THE INVENTION

Presently, there are millions of people around the world who suffer from mild-to-moderate chronic venous insufficiency of the legs. This common condition is characterised by an inadequacy of the venous circulation to return blood from the legs to the heart. The lack of adequate venous return results in venous stasis and an increased pressure within the venous circulation, promoting the development of oedema and tissular water retention.

Chronic venous insufficiency (CVI) is a functional disorder caused by persistent inadequacy of the venous return and is characterised clinically by oedema, skin changes and subjective complaints such as tired, heavy legs, pain or tingling sensations, which are typically amplified by standing upright and by high ambient temperatures. This dysfunction may be a source of major distress with a significant negative impact on the patient's overall well-being and quality of life. Early stages (grade I) are characterised by coronal phlebectasia paraplantaris, subfascial congestion and oedema; grade II CVI is associated with low-grade skin changes, eczema and lipodermatosclerosis. If untreated, grades I and II often progress to an advanced stage characterised by recurrent venous leg ulcers (grade III). The distress caused by the symptoms, even when relatively mild initially, and the risk of later complications call for appropriate supportive and preventive measures to be initiated in the early stages of CVI.

Although some patients, even at early stages, might require surgery (sclerotherapy and variceal surgery), the use of compression stockings with or without additional physiotherapy is the most common treatment approach. The effect of compression is merely mechanical, i.e. this approach does not affect or correct the related biological dysfunction (capillary fragility in particular). Furthermore, the treatment with compression stockings often lacks compliance because of cosmetic concerns and the overall inconvenience of the compressive stockings, in the summer in particular. Therefore there is an urgent need for alternative approaches that are effective, well-tolerated and more convenient.

BRIEF DESCRIPTION OF THE INVENTION

Surprisingly, it has been found that an aqueous extract of red vine leaves can be used for the preparation of a dietary supplement for the prevention and treatment of the discomfort associated with mild-to-moderate chronic venous insufficiency of the lower extremities.

The present invention therefore relates to a method for preventing and/or alleviating the discomfort associated with mild-to-moderate chronic venous insufficiency of the lower extremities, which method comprises administering a dietary supplement containing an aqueous extract of red vine leaves.

Another aspect of the present invention is a dietary supplement composition which comprises an active principle being capable of preventing and/or treating the discomfort associated with mild-to-moderate chronic venous insufficiency of the lower extremities and an pharmaceutically, cosmetically or dietetically acceptable carrier, the improvement wherein is that said active principle essentially consists of an aqueous extract of red vine leaves.

The dietary supplement composition of the present invention preferably consists of herbal ingredients derived by an aqueous extraction from red vine leaves (*folia vitis viniferae*; Extractum Vitis viniferae e folium spissum et siccum) and an acceptable carrier. This extract contains flavon(ol)-glycosides, -glucuronides and flavonoids, with quercetin-3-O-β-D-glucuronide and isoquercitrin (quercetin-3-O-β-glucofuranoside) as its main active ingredients. The range of their pharmacological actions has not yet been fully elucidated, but in-vitro studies indicate that they have antioxidant and anti-inflammatory properties and that they inhibit platelet aggregation and hyaluronidase and reduce oedema, possibly by reducing capillary permeability. Preclinical in-vivo experiments demonstrated anti-inflammatory and capillary wall thickening effects.

DETAILED DESCRIPTION OF THE INVENTION

In a preferred embodiment, the dietary supplement is in a form suitable for oral administration, in particular in a solid dosage form, i.e. a capsule or tablet, that consists of 20 to 60% of aqueous red vine leaf extract with a high flavonoid content of 2–15%. Another preferred dosage form is that of drops containing 3 to 90% of extract. Further suitable administration forms may be coated tablets, syrups, or the like.

With the foregoing in mind, it is a primary object of the present invention to provide a dietary supplement for preventing and alleviating the discomfort associated with mild-to-moderate chronic venous insufficiency of the lower extremities.

It is a further object of the present invention to provide a dietary supplement for preventing and/or alleviating the discomfort associated with mild-to-moderate chronic venous insufficiency of the lower extremities comprising herbal ingredients, wherein the dietary supplement is manufactured pursuant to a controlled process that preserves the herbal curing qualities of the ingredients.

It is still a further object of the present invention to provide a dietary supplement which is effective in preventing and/or alleviating the discomfort associated with mild-to-moderate chronic venous insufficiency of the lower extremities.

It is still a further object of the present invention to provide a dietary supplement for preventing and/or alleviating the discomfort associated with mild-to-moderate chronic venous insufficiency of the lower extremities comprising herbal ingredients and having minimal or no side effects and thus being safe for internal consumption.

A fundamental part of the present invention is the preparation of a supplement for oral administration containing an aqueous extract prepared from dried red vine leaves. The latter is characterised by a high content of 2 to 20%, preferably 2 to 10% of biologically active flavonoids.

In order that this invention be more fully understood, the following examples are set forth. These examples are for the purpose of illustrating embodiments of this invention, and are not to be construed as limiting the scope of the invention in any way.

The examples which follow are illustrative and, as recognized by one skilled in the art, particular conditions could be modified as needed for individual compositions. Materials used in tests below are either commercially available or easily prepared from commercially available materials by those skilled in the art.

The basis of the supplement is the aqueous extract of red vine leaves (foliae vitis viniferae L.). The starting material for the preparation of the extract are red vine leaves collected at a point of time where the content in flavonoids has reached an optimum. This is usually the case around the harvesting time of the grapes. The leaves are carefully dried and crushed. For extraction the leaves are cut to pieces of preferably 5 to 10 mm. To achieve a high content in flavonoids the extraction is done at elevated temperature, preferably at a temperature in the range of 60° to 80° C., over a time of at least 6 up to 10 hours. The preferred method is that of an exhaustive percolation.

The so-called fluid extract obtained in the course of the extraction may be directly used in the preparation of liquid dosage forms. In order to get a more concentrated extract preferably at least part of the solvent is removed by use of a suitable evaporator. The thick extract obtained in this step may again be directly used in the manufacturing of liquid dosage forms.

For the preparation of solid dosage forms the thick extract is dried, for instance by use of a vacuum drying oven or a vacuum drying conveyer. Carriers or excipients may be added during drying to facilitate further processing of the extract. Such carriers or excipients may be silicon dioxide, maltodextrine, glucose syrup, cellulose and others.

The supplement for oral administration is manufactured using usual techniques applied in the food industry or in the pharmaceutical industry. Preferred administration forms are tablets, including coated tablets or capsules. But also liquid preparations, preferably drops, may be chosen.

To prevent and/or alleviate the discomfort of mild-to-moderate chronic venous insufficiency of the lower extremities, the dietary supplement should be taken in dosages corresponding to 80–1000 mg of extract, preferably 300–800 mg, in particular 350–750 mg daily. The total amount of extract may be divided up in 1 to 3 capsules or tablets a day (or an equivalent dose by means of a liquid form). The daily dose should be taken at once, preferably in the morning.

Impressive improvement of the symptoms can be expected within 6 weeks of continuous use. The optimum effect is maintained or amplified on longer use.

In order to verify the effectiveness, safety and tolerability of the dietary supplement of the present invention, a randomised, placebo-controlled, double-blind parallel-group study was conducted in a large and representative sample of patients with evidence of mild-to-moderate chronic venous insufficiency of the lower extremities. This study was carried out in accordance with the Declaration of Helsinki and the Principles of Good Clinical Practice. The results are set forth below:

Objective—To assess the efficacy and safety of once-daily doses of 360 and 720 mg red vine leaf extract (RVLE) compared to placebo in patients with grade I and incipient grade II chronic venous insufficiency (CVI).

Design—A 12-week, randomised, double-blind, placebo-controlled, parallel-group, multi-center study.

Patients—Male and female outpatients between 25 and 75 years of age with grade I and grade II CVI (i.e. without extensive trophic changes), without further significant medical conditions and not treated with compression stockings, diuretics or other drugs affecting fluid balance.

Intervention—Patients were randomly assigned to a double-blind treatment with placebo, 360 mg RVLE or 720 mg RVLE once daily for 12 weeks, preceded and followed by a single-blind 2-week placebo treatment for baseline run-in and end-of-trial washout, respectively. Study criteria were evaluated at baseline, after 6 and 12 weeks of treatment and 2 weeks after discontinuation of treatment.

Outcome Measures—Primary outcome measure: Change in lower leg volume, as determined by water displacement plethysmography. Secondary outcome measures: Change in ankle and calf circumference; change in intensity of key symptoms ("tired, heavy legs", "feeling of tenseness", "tingling sensation", and "tenderness/pain") compared to baseline.

Results—Of the 260 patients enrolled and randomised, 219 completed the study in accordance with the protocol. In the intention-to-treat analysis (N=257), the mean (±SD) lower leg volume of the patients treated with placebo (N=87) increased by 15.2±90.1 g (displaced water mass) compared to baseline after 6 weeks of treatment and by 33.7±96.1 g compared to baseline after 12 weeks of treatment. In patients treated with RVLE according to this invention, however, lower leg volume decreased and, after 12 weeks of treatment, the difference in mean lower leg volume between the active treatment groups and the placebo group was −75.9 g (95% CI: −106.1 to 45.8 g) for the 360-mg RVLE group (N=86) and −99.9 g (95% CI: −130.3 to −69.6 g) for the 720-mg RVLE group (N=84). The changes in calf circumference showed a similar pattern; in patients treated with RVLE, both the higher dose (720 mg) and, to a lesser extent, the lower dose (360 mg) resulted in a clear reduction in circumference over time, whereas, in patients treated with the placebo, the circumferences remained largely unchanged (95% CI of the estimated treatment effects vs. placebo after 12 weeks: −1.40 to −0.56 cm for 360 mg RVLE and −1.73 to −0.88 cm for 720 mg RVLE). The reductions in ankle circumference were qualitatively similar but quantitatively less marked.

There was a clear improvement in key CVI symptoms at 6 weeks with all treatments, but a further improvement at week 12 was seen only in the active treatment groups; at 12 weeks, the changes compared to baseline were significantly greater (p<0.001) in both active treatment groups than in the placebo group. The treatments were well tolerated. Adverse events were rare and usually mild. Two AEs during treatment with the placebo led to hospitalisation. Three further patients were withdrawn because of AEs which occurred during treatment with the placebo.

Conclusion—Once-daily doses of 360 and 720 mg RVLE appeared safe and effective in the treatment of mild CVI, reducing lower leg oedema and circumference whilst improving key CVI-related symptoms. The extent of oedema reduction is at least equivalent to that reported for compression stockings and/or other oedema-reducing agents. The higher dose was as well tolerated as the lower dose but resulted in a slightly greater and more sustained improvement.

It will be readily apparent to those skilled in the art that various changes and modifications of an obvious nature may be made without departing from the spirit of the invention, and all such changes and modifications of an obvious nature may be made without departing from the spirit of the invention, and all such changes and modifications are considered to fall within the scope of the invention, as defined by the claims as defined. While the composition of the present invention has been set forth in what is believed to be preferred embodiments, it is recognised that departures may be made within the spirit and scope of the following claims which, therefore, should not be limited except within the doctrine of equivalents.

What is claimed is:

1. A composition consisting of: (1) an active principle consisting essentially of an aqueous extract of red vine leaves comprising 2 to 20% flavonoids and less than about 0.15% anthocyanins, and (2) a pharmaceutically, cosmetically, or dietetically acceptable carrier; wherein said aqueous extract of red vine leaves is obtainable by a method comprising the steps of:

(a) collecting red vine leaves at a point of time when the content in flavonoids has reached an optimum;
(b) drying and crushing the leaves;
(c) cutting the leaves to pieces;
(d) extracting the leaves with water at temperatures from 60 to 80° C. for 6 to 10 hours in an exhaustive percolation; and, optionally,
(e) concentrating the obtained extract.

2. The composition according to claim 1, wherein the active principle is present in an amount that is about 20 to 60% of the total mass of the composition.

3. The composition according to claim 1, wherein the flavonoids are present in an amount that is about 2 to 10% of the total mass of the active principle.

4. The composition according to claim 1, wherein the flavonoids are present within the range of 1% to 10% relative to the total mass of the composition.

5. The composition according to claim 1, wherein the aqueous extract of red vine leaves comprises quercetin-3-O-β-D-glucuronide and isoquercitrin (quercetin-3-O-β-glucofuranoside).

6. The composition according to claim 1, which contains more than about 18.0% polyphenois.

7. The composition according to claim 1, which is in the form of granules, tablets, capsules, drops or syrups.

8. The composition according to claim 1, wherein the flavonoids are present in an amount that is about 2 to 15% of the total mass of the active principle.

* * * * *